United States Patent
Feldman

(10) Patent No.: US 10,285,776 B1
(45) Date of Patent: May 14, 2019

(54) UNITARY CORDLESS DENTAL DRIVE APPARATUS

(71) Applicant: Michael Feldman, Toms River, NJ (US)

(72) Inventor: Michael Feldman, Toms River, NJ (US)

( * ) Notice: Subject to any disclaimer, the term of this patent is extended or adjusted under 35 U.S.C. 154(b) by 205 days.

(21) Appl. No.: 15/393,492

(22) Filed: Dec. 29, 2016

Related U.S. Application Data

(60) Provisional application No. 62/298,493, filed on Feb. 23, 2016.

(51) Int. Cl.
*A61C 1/00* (2006.01)
*A61C 1/06* (2006.01)

(52) U.S. Cl.
CPC ............ *A61C 1/0053* (2013.01); *A61C 1/003* (2013.01); *A61C 1/0023* (2013.01); *A61C 1/06* (2013.01); *A61C 2204/002* (2013.01); *A61C 2204/005* (2013.01)

(58) Field of Classification Search
CPC ..... A61C 1/0053; A61C 1/0023; A61C 1/003; A61C 1/06; A61C 2204/002; A61C 2204/005; A61C 1/02
See application file for complete search history.

(56) References Cited

U.S. PATENT DOCUMENTS

| | | | | |
|---|---|---|---|---|
| 3,827,149 A | * | 8/1974 | Brennan | B23B 45/00 433/106 |
| 3,855,704 A | * | 12/1974 | Booth | A61C 1/0023 251/63 |
| 5,039,304 A | * | 8/1991 | Heil | A61C 1/18 433/126 |
| 6,014,679 A | * | 1/2000 | Tomioka | G06F 16/954 715/201 |
| 6,722,881 B1 | * | 4/2004 | Altendorf | A61C 1/0038 433/101 |
| 7,428,439 B1 | * | 9/2008 | Reynolds | G06F 3/0383 318/400.18 |
| 8,159,370 B2 | * | 4/2012 | Shields | A61B 1/00016 341/20 |
| 8,274,376 B2 | * | 9/2012 | Shields | A61B 5/7475 340/12.5 |
| 8,692,657 B2 | * | 4/2014 | Villette | G05G 1/30 200/86.5 |
| 8,725,096 B2 | * | 5/2014 | Lint | A61C 1/0015 455/161.2 |
| 8,937,561 B2 | * | 1/2015 | Shields | G05B 11/01 341/20 |
| 9,265,518 B2 | * | 2/2016 | Ware | A61B 17/32002 |
| 9,585,549 B1 | * | 3/2017 | Elazar | A61B 1/247 |

(Continued)

*Primary Examiner* — Nicholas D Lucchesi

(74) *Attorney, Agent, or Firm* — Michael R. Philips

(57) ABSTRACT

The invention provides a unitary cordless dental drive apparatus with a cantilever arm extending outward and positioned to allow a dental nose cone to be connected. An activating switch is located at the free end of the cantilever arm in a position that is convenient for manipulation by a user. In a second embodiment, the switch is in the form of a contactor mounted below the cantilever arm to contact the nose cone when pressed. In a third embodiment, a foot pedal connected to a wireless transmitter is provided to send a signal to a receiver located within the handpiece for activating the handpiece.

8 Claims, 4 Drawing Sheets

(56) References Cited

U.S. PATENT DOCUMENTS

| | | | |
|---|---|---|---|
| 2007/0166662 A1* | 7/2007 | Lint | A61C 17/20 |
| | | | 433/101 |
| 2007/0254261 A1 | 11/2007 | Rosenblood et al. | |
| 2008/0017787 A1* | 1/2008 | Okawa | A61B 1/0615 |
| | | | 250/226 |
| 2008/0140158 A1* | 6/2008 | Hamel | A61B 17/32002 |
| | | | 607/60 |
| 2008/0166685 A1* | 7/2008 | Rosenblood | A61C 1/0015 |
| | | | 433/101 |
| 2009/0081610 A1* | 3/2009 | Hayman | A61C 17/005 |
| | | | 433/125 |
| 2011/0275025 A1* | 11/2011 | Lint | A61C 1/0015 |
| | | | 433/27 |

* cited by examiner

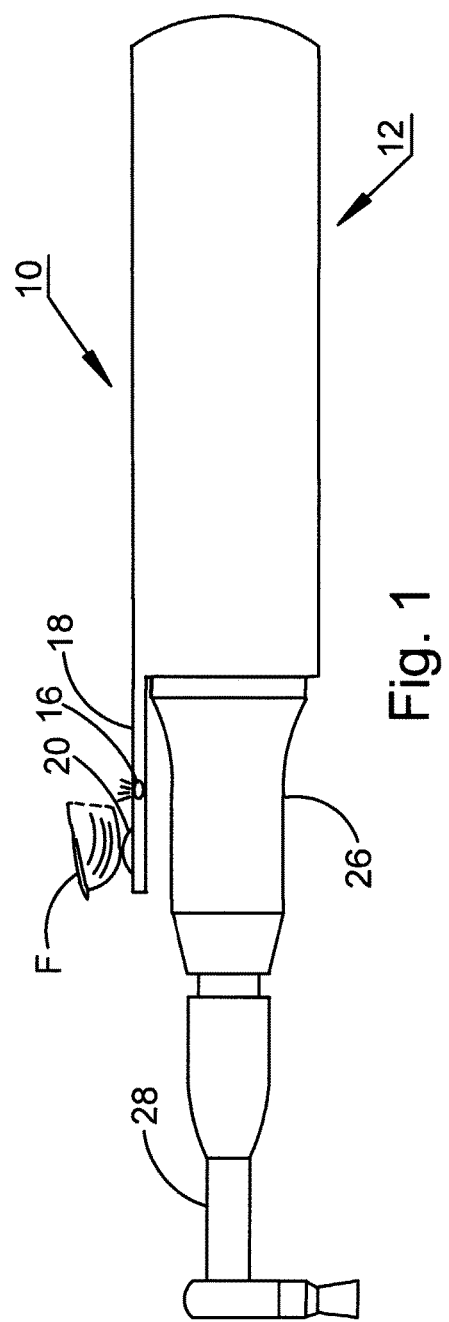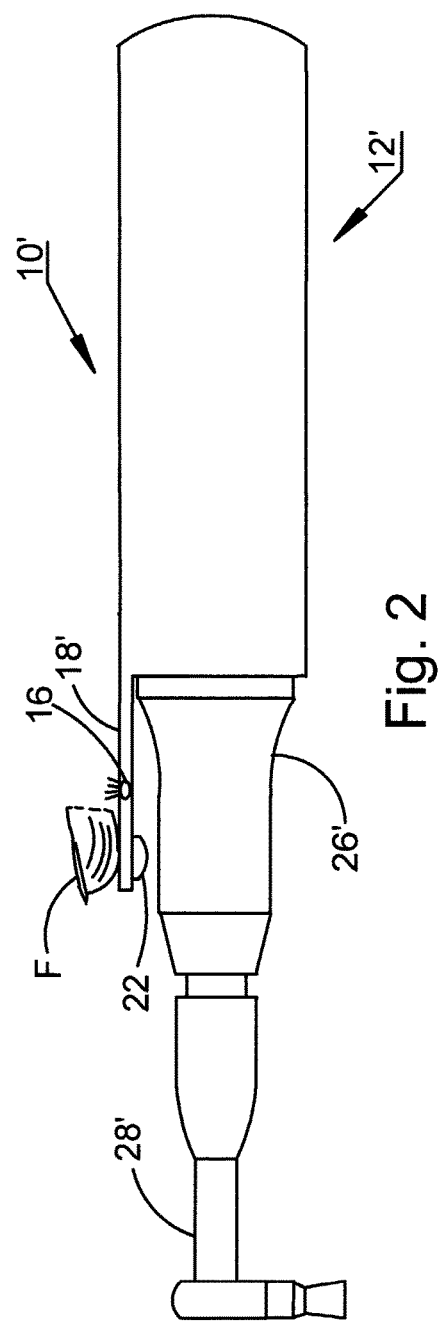

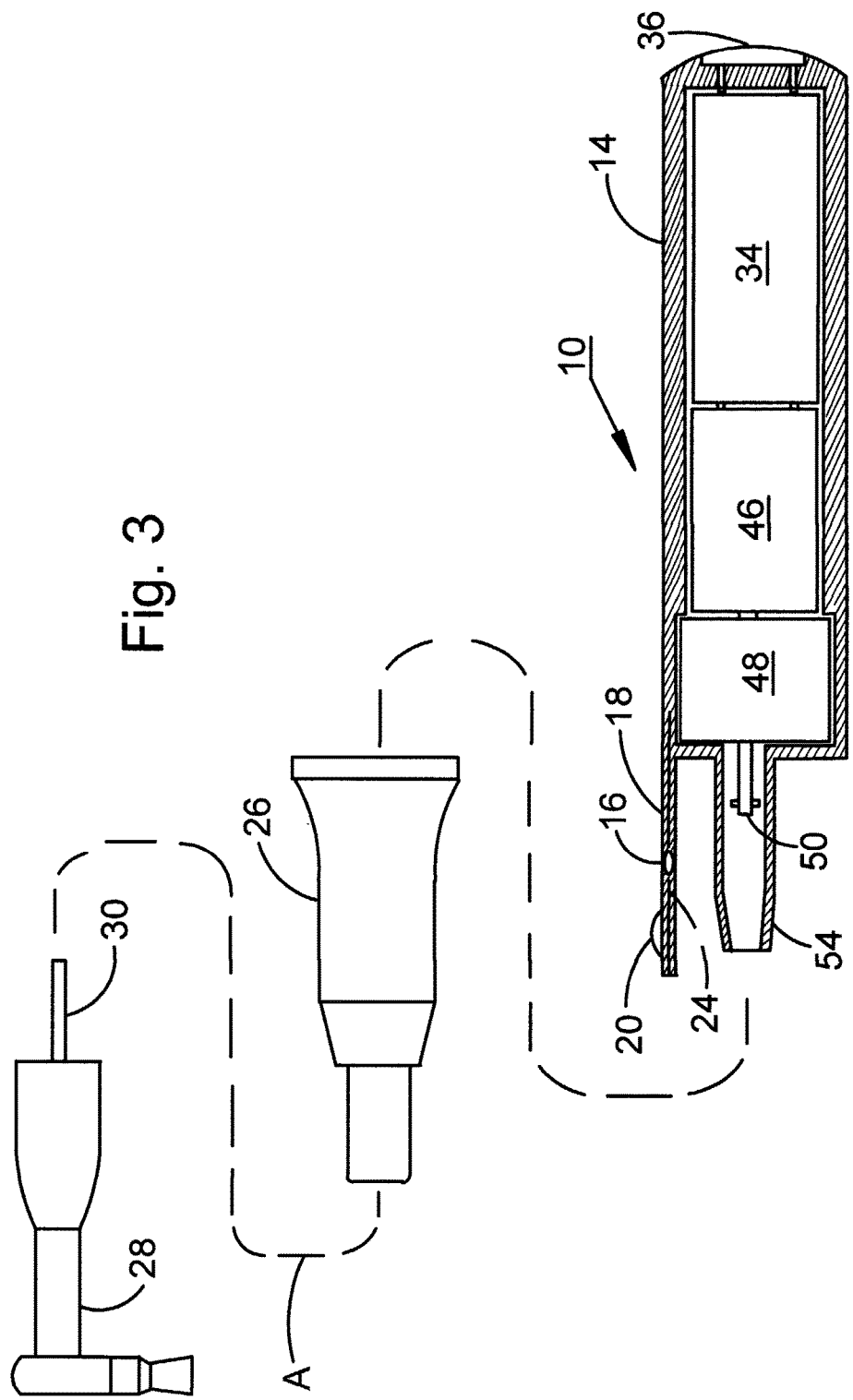

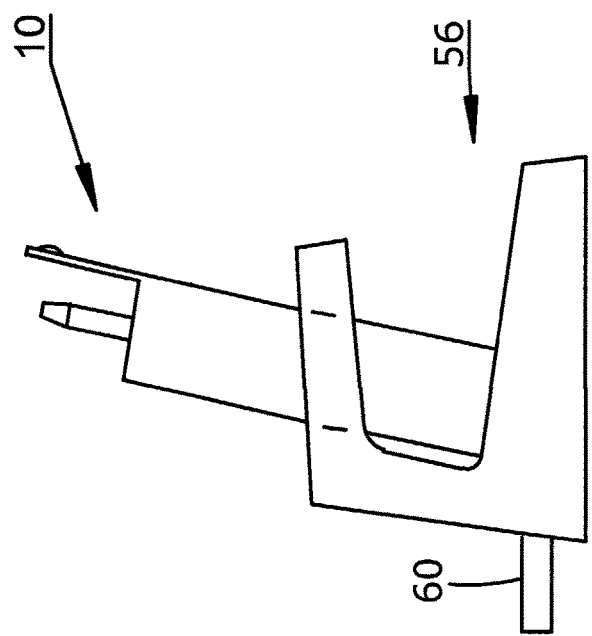
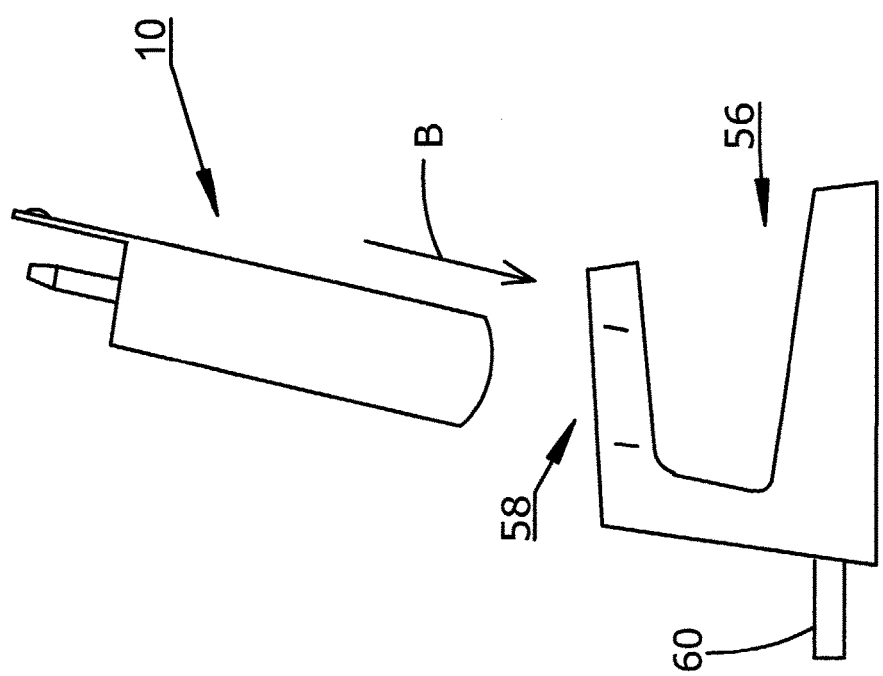

UNITARY CORDLESS DENTAL DRIVE APPARATUS

RELATED APPLICATION

This application is a conversion and retains priority of provisional patent application No. 62/298,493 filed Feb. 23, 2016.

FIELD OF THE INVENTION

The present invention relates to the field of dental equipment, and more particularly to a dental cordless drive apparatus incorporating a rechargeable battery power source and a cantilevered activating switch.

BACKGROUND OF THE INVENTION

The practice of dentistry utilizes a plurality of power driven tools for remediating decayed dental areas and for cleaning tooth surfaces. Traditional dental equipment is driven by an external drive device to cause the tool to rotate. The external drive device may be either a motor with an articulable power transmission, e.g. a pivoting pulley and belt system, a supply of compressed air that is directed to the dental handpiece through tubing, or an electric motor in the dental handpiece that is powered by an electrical cord. These three drive systems provide the needed power, but the connected hoses, pulleys and belts, or electrical cords cause them to be fairly cumbersome and fatiguing to use, particularly for extended periods of time, as is typically the case in professional cleaning of a patient's teeth.

Recent developments in dental equipment have provided certain advances in apparatus for the rotating of dental tools. These drive devices are substantially self-contained and free of a cumbersome external drive. These devices have a battery and a motor within the handpiece, thereby eliminating the cumbersome power transmission apparatus. The resultant cordless handpiece is more easily manipulated and, especially in use by a dentist or dental hygienist for long periods during dental cleanings, less likely to cause fatigue. However, the known devices are limited in the manner for controlling the power, i.e. switched on and off. The known cordless handpieces are controlled by a switch that is located in an inconvenient position. The switch on known devices is located either toward the rear of the handpiece or near the front of the handpiece. The dental hygienist must hold the handpiece with one hand and actuate the switch with the other hand, typically done before the dental tool is in the patient's mouth. When used for cleaning the patient's teeth, this results in much of the cleansing paste being sprayed outside of the mouth, which tends to be wasteful and messy. In addition, tooth cleaning is typically done with a series of short bursts of drive power, making the remotely located switch even more inconvenient. In order to rotate the dental tool at the forward end of the handpiece, the entire handpiece must be rotated. The present invention provides a unitary cordless dental drive apparatus that is an improvement on, and overcomes the drawbacks of, the known prior devices.

SUMMARY OF THE INVENTION

The invention disclosed below provides a unitary cordless dental drive apparatus adapted for flexible, comfortable, and durable dental office service. The novel handpiece has a battery power source, a drive motor and a gear train enclosed in a housing. The housing is split to enable opening for factory servicing. A European type (E-type) output shaft extends from the gear train, allowing all universal dental nose cones and tools to be connected. The battery power is connected to the motor through a switch which, in the first preferred embodiment, is supported at the free end of a cantilever arm and located in a position to be convenient for the user. The invention includes a microprocessor, or programmable logic control, enabling a variety of functions for the switch, e.g. on/off, momentary contact, timed cycle on with automatic off, varying operating speed by steps each time the switch is pressed. The cantilever arm may be internally reinforced by a resilient wire. In a second embodiment of the invention, a cantilever arm is incorporated with an electrically conductive contactor, the arm adapted for flexing under pressure to cause the contactor to touch a conductive part of the dental nose cone to activate the drive motor. In a third embodiment of the invention, a wireless receiver is included within the dental handpiece. A wireless transmitter is mounted to an output of pressurized air from a standard dental foot pedal. The dental handpiece of the present invention is wirelessly activated and controlled for speed by the application of pressure on the standard existing dental foot pedal, causing the wireless transmitter to send a signal to the wireless receiver. The wireless receiver is directly in control of the handpiece motor. In all embodiments of the invention, the dental handpiece is fully operable with no directly connected air hoses or drive belts and pulleys.

BRIEF DESCRIPTION OF THE DRAWINGS

The present invention is best understood in conjunction with the accompanying drawing figures in which like elements are identified by similar reference numerals and wherein:

FIG. 1 is a side elevation view of the unitary cordless dental drive apparatus in a first embodiment.

FIG. 2 is a side elevation view of the unitary cordless dental drive apparatus in a second embodiment.

FIG. 3 is an exploded side elevation view of the embodiment of FIG. 1 with the dental handpiece illustrated in cross section.

FIGS. 4A and 4B are side elevation views of the cordless drive apparatus being placed into a charging base and set into the charging base.

DETAILED DESCRIPTION OF THE PREFERRED EMBODIMENTS

Figure 5:
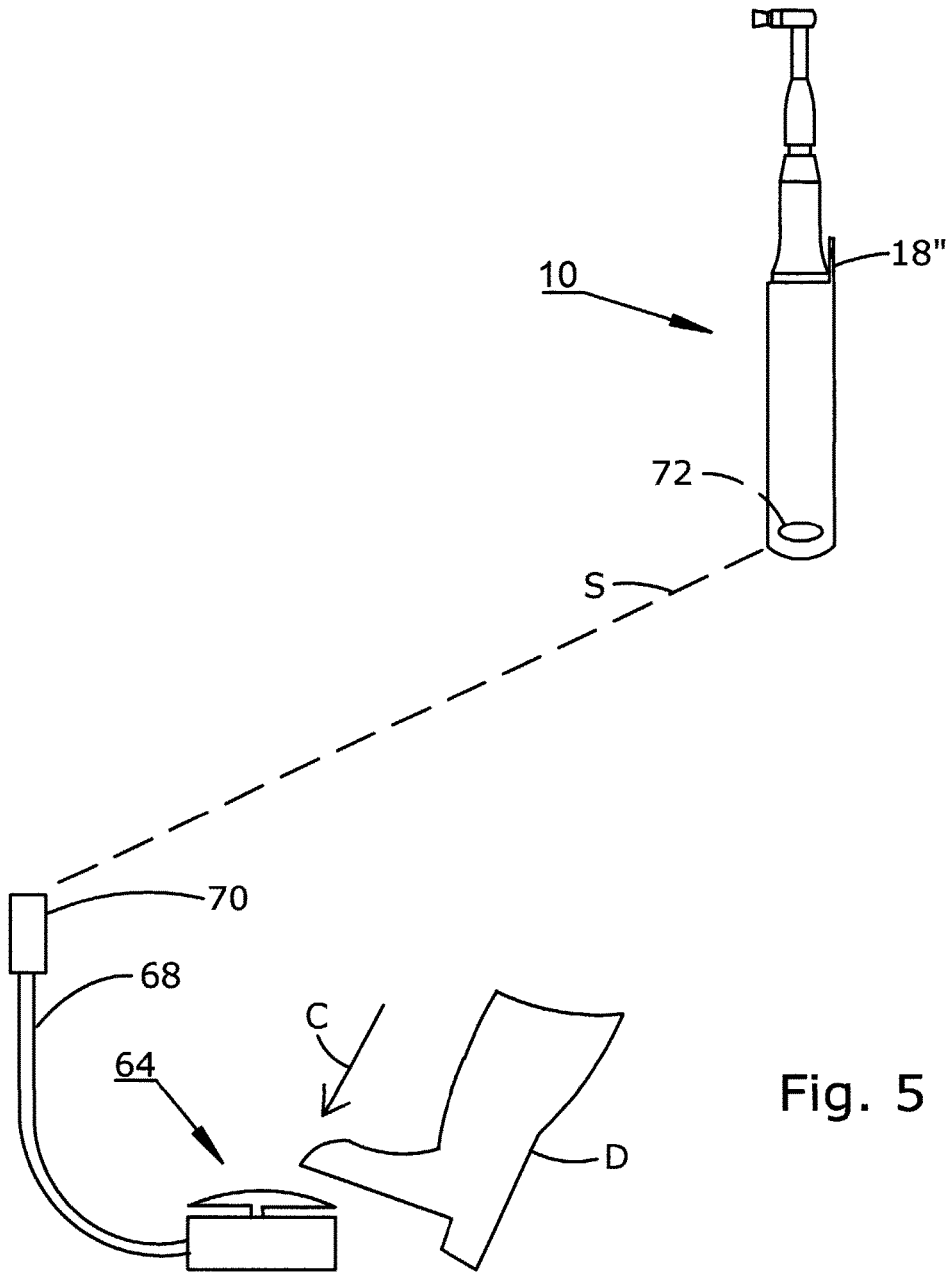
FIG. 5 is a schematic view of a third embodiment of the invention in which power is controlled by an existing dental foot-operated pedal and sent wirelessly from a transmitter to a receiver in the dental handpiece.

Referring to FIG. 1, a first embodiment of the present invention is shown in side elevation view. The unitary cordless dental drive apparatus is designated handpiece 10. Handpiece 10 includes a power unit 12, e.g. a rechargeable battery, a power converter unit including a motor and a gear train. The internal components of handpiece 10 are preferably encased in a sealed housing for protection against moisture and contamination. A conventional dental nose cone 26 is removably mounted to handpiece 10. Nose cone 26 receives power from power unit 12 to rotatably drive a prophylaxis angle device 28. It will be understood that the present invention may be beneficially utilized with non-disposable prophylaxis angle devices as well as disposable ones. Depending on the purpose for which the present invention is to be used, another dental attachment may be employed, e.g. an abrasive tip. A switch 20 is mounted to the free end of an arm 18, arm 18 being fixedly assembled in cantilever fashion to the housing portion of handpiece 10 to position switch 20 conveniently for being contacted by a user's fingertip F when in use. Arm 18 is configured as a cantilever structure to suspend switch 20 and maintain a space between arm 18 and nose cone 26, permitting nose cone 26 to be readily mounted and removed. Switch 20 is preferably in the form of a micro-miniature membrane switch that is connected to a microprocessor (not shown) within handpiece 10, the microprocessor including a transistor relay activated by switch 20. When activated, the transistor relay connects the enclosed battery power source to the motor, causing the cleansing paste cup of prophylaxis angle device 28 to rotate. Switch 20 also activates an indicator 16, e.g. a miniature LED light source. Indicator 16 may be programmed to remain continuously on, flash on in a specified pattern, as well as display different colors for different conditions, e.g. normal operation, excessive power being drawn from the power source, or the power source in need of recharging, etc. As will be understood by those skilled in the trade, the location of switch 20 at the free end of cantilever arm 18 allows the dental hygienist to place the tip of prophylaxis angle device 28 inside the mouth of the patient before activating power unit 12, thereby avoiding spraying and waste of the cleansing paste.

Referring now to FIG. 2, a second embodiment of the present invention is shown in side elevation view. Handpiece 10', power unit 12', nose cone 26', and prophylaxis angle device 28', are substantially similar to comparable components in the first embodiment shown in FIG. 1. A cantilever arm 18' extends outwardly from handpiece 10'. The second embodiment of FIG. 2 differs from the first embodiment of FIG. 1 in that the electrical circuit is completed by a contactor 22 mounted to the lower surface of arm 18'. As nose cone 26' is typically metallic, when the user presses arm 18' to flex downward with fingertip F to cause contactor 22 to touch nose cone 26', a circuit is closed between the battery and the motor. As will be described below, cantilever arm 18' of this second embodiment is designed to be flexed by finger pressure. This second embodiment of the invention also incorporates the primary objective of locating contactor 22 for convenient use by the dental hygienist during tooth cleaning or other functions.

Referring now to FIG. 3, the unitary cordless dental drive apparatus of the first embodiment is shown with the components arrayed in exploded side elevation view. The components are in position to be assembled along axis A, shown as a dashed line. Handpiece 10 is shown in cross section for clarity. Handpiece 10 has a unitary housing 14 with cantilever arm 18 molded integrally therewith. Arm 18 may, optionally, be reinforced to withstand flexural stress with the incorporation of one or more reinforcing rods 24, e.g. piano wire. Indicator 16 is also molded into arm 18 and incorporated in the electrical circuit of handpiece 10. Electrical power is provided by a battery 34 to a motor 46 which is mechanically coupled to a gear train 48 for driving an output shaft 50 at a selected rotary speed and torque. Battery 34 may be either a rechargeable or non-rechargeable replaceable type. Gear train 48 may be configured to provide continuous rotary action or reciprocating rotary action according to the intent of the manufacturer. Output shaft 50 with coupler 54 and nose cone 26 are in the configuration known in the trade as an E-type coupling to connect securely to one another. In the preferred embodiment of the invention, coupler 54 is sized to fit slidingly into nose cone 26, allowing the user to swivel nose cone 26 and prophylaxis angle device 28 while keeping handpiece 10 upright with switch 20 at the fingertip position. Prophylaxis angle device 28 is mounted to nose cone 26 and driven through nose cone 26 by shaft 50. Battery 34 is preferably a rechargeable battery with an operating rating of 650 milliampere hours at 3.7 volts. Handpiece 10 includes a charging connector 36 that is configured to operatively engage a charging base device when battery 34 is in need of being recharged.

Referring further to FIG. 3, arm 18 extends outwardly from handpiece 10 in cantilever fashion to position switch 20 suspended at a convenient placement for being manipulated by finger pressure of the user. In the preferred embodiments of the invention, housing 14 of handpiece 10 is formed of a light weight material, e.g. high density polyethylene. Whereas the plastic encased handpiece is not receptive to repeated autoclaving, and whereas only the nose cone 26 and prophylaxis angle device 28 contact the mouth of the patient, it is not generally necessary to autoclave handpiece 10. Handpiece 10 may be adequately protected by applying a thin sleeve over the handpiece prior to the prophylactic procedure and/or cleaning by use of a disinfecting solution. The dental tool, specifically the disposable prophylaxis angle device 28, is discarded after use. In the first embodiment of the invention, metallic reinforcing bars 24, shown within cantilever arm 18, are sized to maintain the structural rigidity of arm 18 against finger pressure on switch 20. Reinforcing bars 24 also serve to conduct electrical current from power source battery 34 through switch 20 to motor 46. It is understood in the second embodiment of the invention (see FIG. 2) that reinforcing rods 24 shown in FIG. 3 in arm 18 are sized to be resilient and spring back to the original shape. The placement of switch 20 on cantilever arm 18 allows nose cone 26 or other dental attachments to be assembled and removed from coupler 54 while locating switch 20 for comfortable use by the dental hygienist.

The unitary cordless dental drive apparatus of the invention is for use by dentists and dental hygienists, some of whom may apply excessive force of the cleaning cup of the prophylaxis angle device against the patient's teeth. This excessive pressure places a strain on the motor, potentially causing motor damage. Excessive pressure against the teeth may also cause damage to the enamel. To avoid enamel damage and motor damage, an additional feature of the invention is to incorporate an overload restriction control in the microprocessor that is built into the handpiece. When an excessive current, e.g. 1.0 amp, is drawn, electrical current is automatically deactivated and a signal is energized such as light 16 or a buzzer. By deactivating the electrical current and stopping the motor, the dentist or dental hygienist will soon learn the appropriate degree of pressure to apply.

Referring now to FIG. 4A, a side elevation view is shown of handpiece 10 about to be inserted into a recharge unit 56. Recharge unit 56 receives electrical power through power cord 60. Recharge unit 56 is formed with an aperture 58 for receiving handpiece 10 slidingly therethrough.

Referring now to FIG. 4B, handpiece 10 is shown as being inserted into recharge unit 56 for a prescribed period to recharge the battery within handpiece 10. While handpiece 10 is illustrated in recharge unit 56 without the dental nose cone or dental tool, recharging may be accomplished equally with or without these components.

Referring now to FIG. 5, a third embodiment of the present invention is shown in schematic side elevation view. In this embodiment, the previously described on-board switch has been eliminated from handpiece 10 and an existing foot control 64 is employed to activate and deactivate the motor drive within handpiece 10. The cantilever arm 18″ is relatively shorter in this embodiment and includes a signal but no switch. In the typical dental office application of the invention, foot control 64 is connected to receive a supply of pressurized air (not shown). An air hose 68 is connected to an output port of foot control 64 to conduct pressurized air to a wireless transmitter 70. The degree of pressure and flow of air being conducted through foot control 64 to transmitter 70 varies according to the action of the dental hygienist in the direction indicated by arrow C, the dentist or dental hygienist represented by boot D. Transmitter 70 incorporates a pressure sensitive switch and any form of wireless transmitter. Transmitter 70 receives the pressurized air and transmits a wireless signal S to a wireless receiver 72 that is contained within handpiece 10 and connected internally to the microprocessor and relay therewithin. As described above, the internal microprocessor activates and controls the speed, direction, and duration of action of the dental tool connected to handpiece 10.

While the description above discloses preferred embodiments of the present invention, it is contemplated that numerous variations and modifications of the invention are possible and are considered to be within the scope of the claims that follow.

What is claimed is:

1. A unitary cordless dental drive apparatus, comprising:
   a. a handpiece having a housing;
   b. a power source contained within the housing;
   c. an electric motor mechanically connected to a gear train, the motor and gear train contained within the housing;
   d. an output shaft connected to the motor and gear train and extending outward of the housing;
   e. a hollow coupler formed integrally with the housing in a location to surround the output shaft;
   f. a foot pedal control connected to a supply of pressurized air and having a pressurized air output port;
   g. a wireless transmitter connected to receive pressurized air through the output port of the foot pedal control to cause the wireless transmitter to transmit a wireless signal in proportion to a flow of air from the foot pedal control; and
   h. within the handpiece, a wireless receiver connected to a relay for conveying power from the power source to the electric motor;
   i. wherein when the foot pedal control is pressed, the wireless transmitter sends a wireless signal to the wireless receiver activating the relay to complete a circuit from the power source to the electric motor to activate the electric motor.

2. The unitary cordless dental drive apparatus according to claim 1, wherein the power source comprises a battery.

3. The unitary cordless dental drive apparatus according to claim 1, wherein the output shaft comprises an E-type shaft for connecting to an E-type socket within the nose cone.

4. A unitary cordless dental drive apparatus, comprising:
   a. a handpiece having a housing;
   b. a power source and a drive device contained within the housing;
   c. an output shaft connected to the drive device and extending outward of the housing;
   d. a hollow coupler formed integrally with the housing in a location to surround the output shaft;
   e. a foot pedal control connected to a supply of pressurized air and having a pressurized air output port;
   f. a wireless transmitter connected to receive pressurized air through the output port of the foot pedal control to cause the wireless transmitter to transmit a wireless signal; and
   g. within the housing, a wireless receiver connected to a relay for conveying power from the power source to the drive device;
   h. wherein when the foot pedal control is pressed, the wireless transmitter sends a wireless signal to the wireless receiver, activating the relay to complete a circuit from the power source to the drive device to activate the drive device.

5. The unitary cordless dental drive apparatus according to claim 4, wherein the drive device comprises an electric motor mechanically connected to a gear train.

6. The unitary cordless dental drive apparatus according to claim 4, wherein the power source comprises a battery.

7. The unitary cordless dental drive apparatus according to claim 4, wherein the output shaft comprises an E-type shaft for connecting to an E-type socket within the nose cone.

8. The unitary cordless dental drive apparatus according to claim 4, wherein the wireless transmitter is responsive to variations in air pressure.

* * * * *